(12) United States Patent
Tanaka et al.

(10) Patent No.: US 8,008,526 B2
(45) Date of Patent: Aug. 30, 2011

(54) SYNTHESIS REACTION CATALYST AND METHOD OF SYNTHESIZING COMPOUND USING THE SAME

(75) Inventors: Hirohisa Tanaka, Shiga (JP); Kimiyoshi Kaneko, Tokyo (JP)

(73) Assignee: Nitto Denko Corporation, Osaka (JP)

( * ) Notice: Subject to any disclaimer, the term of this patent is extended or adjusted under 35 U.S.C. 154(b) by 896 days.

(21) Appl. No.: 11/886,540

(22) PCT Filed: Mar. 16, 2006

(86) PCT No.: PCT/JP2006/305204
§ 371 (c)(1),
(2), (4) Date: Sep. 17, 2007

(87) PCT Pub. No.: WO2006/098396
PCT Pub. Date: Sep. 21, 2006

(65) Prior Publication Data
US 2009/0023943 A1    Jan. 22, 2009

(30) Foreign Application Priority Data
Mar. 17, 2005  (JP) ................................ 2005-077800

(51) Int. Cl.
*C07C 63/33* (2006.01)
(52) U.S. Cl. ............. 562/492; 556/136; 556/7; 554/220
(58) Field of Classification Search .................. None
See application file for complete search history.

(56) References Cited

U.S. PATENT DOCUMENTS

| | | | |
|---|---|---|---|
| 7,411,082 B2 * | 8/2008 | Ley et al. ................ | 556/136 |
| 2005/0215804 A1 * | 9/2005 | Ley et al. ................ | 554/220 |

FOREIGN PATENT DOCUMENTS

| | | |
|---|---|---|
| EP | 1 533 274 A1 | 5/2005 |
| EP | 1 728 766 A1 | 12/2006 |
| WO | WO 2004/005194 | 1/2004 |
| WO | WO 2005/090238 | 9/2005 |

OTHER PUBLICATIONS

Takatoshi Ito et al., "Palladium-Catalyzed Cross-Coupling Reaction of Potassium Diaryldifluoroborates with Aryl Halides," Synlett, 2003, pp. 1435-1438, No. 10, Georg Thieme Chemistry, New York.
Olivier Baudoin et al., "Application of the Palladium-Catalyzed Borylation/Suzuki Coupling (BSC) Reaction to the Synthesis of Biologically Active Biaryl Lactams," Journal of Organic Chemistry, 2002, pp. 1199-1207, vol. 67, ACS Publications.
Stephen P. Andrews et al., "Heterogeneous or Homogeneous? A Case Study Involving Palladium-Containing Perovskites in the Suzuki Reaction," Advanced Synthesis & Catalysis, 2005, pp. 647-654, vol. 347, Wiley, Weinheim.
Isao Tan et al., "Structural Stability of Pd-Perovskite Catalysts after Heat Treatment Under Redox Condition," Journal of the Ceramic Society of Japan, 2005, pp. 71-76, vol. 113, Japan.
Tan, I et al., Structural Stability of Pd-Perovskite Catalysts after Heat Treatment Under Redox Condition, Journal of the Ceramic Society of Japan, 2005, vol. 113, No. 1313.
Martin D. Smith et al., Palladium-containing perovskites: recoverable and reuseable catalysts for Suzuki couplings, Chem. Comm., 2003, No. 21, UK.
Y. Nishihata et al., Self-regeneration of a Pd-perovskite catalyst for automotive emissions control, Nature, vol. 418, No. 6894, pp. 164-167, Jul. 2002, Japan.

* cited by examiner

*Primary Examiner* — Sudhakar Katakam
(74) *Attorney, Agent, or Firm* — Jean C. Edwards, Esq.; Edwards Neils PLLC

(57) ABSTRACT

To improve a catalytic activity of a composite oxide, to carry out a reaction in a high yield, and to provide a synthesis reaction catalyst having excellent handling properties and a method of a synthesizing a compound using the same, a synthesis reaction catalyst containing a palladium-containing perovskite-type composite oxide having a specific surface area of 0.5 to 9.5 $m^2/g$ is used in Suzuki Cross-Couplings given by the following general scheme (14).

[Chemical Formula 4]

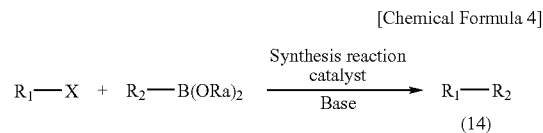

(14)

2 Claims, No Drawings

SYNTHESIS REACTION CATALYST AND METHOD OF SYNTHESIZING COMPOUND USING THE SAME

The present invention is a 35 USC 371 national stage entry of PCT/JP2006/0305204, filed Mar. 16, 2006 which claims priority from Japanese Patent Application No. 2005-077800, filed Mar. 17, 2005, the contents of which are herein incorporated by reference in their entirety.

The present invention relates to a synthesis reaction catalyst and a method of synthesizing a compound using the same and, more particularly, to a synthesis reaction catalyst including a perovskite-type composite oxide containing palladium, and a method of a synthesizing compound through a coupling reaction using the same.

BACKGROUND OF THE INVENTION

There have hitherto been proposed various examples of the reaction of a catalyst containing palladium as active species, and it is reported that a catalyst including a palladium-containing perovskite-type composite oxide is highly active as a coupling reaction catalyst, and that also the catalyst can be recovered and reused after the completion of the reaction (see the following Non Patent Document 1).

A palladium-containing perovskite-type composite oxide described in the following Non Patent Document 1 is, for example, a composite oxide represented by $La_{1.00}Fe_{0.57}Co_{0.38}Pd_{0.05}O_3$, and the composite oxide can be obtained by baking a precursor of the composite oxide including $La_{1.00}Fe_{0.57}Co_{0.38}Pd_{0.05}O_3$ at 700° C. for 4 hours (see the following Non Patent Document 2).

Non Patent Document 1: Martin D. Smith et al., Chemical Communications, pp. 2652-2653, 7 Nov., 2003

Non Patent Document 2: Y. Nishihata et al., Nature, Vol. 418, No. 6894, pp. 164-167, 11 Jul., 2002

DISCLOSURE OF THE INVENTION

However, in preparation of the perovskite-type composite oxide of $La_{1.00}Fe_{0.57}Co_{0.38}Pd_{0.05}O_3$, when the precursor is baked at 700° C. for 4 hours, a specific surface area of the perovskite-type composite oxide obtained by baking the precursor becomes approximately 20 m²/g.

Further, in a solid catalyst, a catalytic activity is commonly proportional to a specific surface area of a catalyst, so that if a specific area of the perovskite-type composite oxide is adjusted to 20 m²/g or more, a catalytic activity is improved in a coupling reaction and thus synthesis in a high yield is expected.

However, even if a specific area of the perovskite-type composite oxide is adjusted to more than 20 m²/g, synthesis in a high yield is not achieved and, to the contrary, there arises a problem that the yield decreases.

There is also a problem that when a specific area of a catalyst increases, individual catalytic particles become smaller and thus handling properties deteriorates so that the catalyst cannot be efficiently recovered after the completion of the reaction.

An object of the present invention is to provide a synthesis reaction catalyst which improves an activity of a perovskite-type composite oxide, permits synthesis of a compound in a high yield and is excellent in handling properties, and a method of a synthesizing a compound using the same.

SUMMARY OF THE INVENTION

To achieve the above object, the synthesis reaction catalyst of the present invention comprises a palladium-containing perovskite-type composite oxide represented by the general formula (1):

$$A_xB_{(1-y)}Pd_yO_{3+\sigma} \tag{1}$$

wherein A represents at least one element selected from rare earth elements and alkaline earth metals; B represents at least one element selected from transition elements (excluding rare earth elements and Pd) and Al; x represents an atomic ratio satisfying the following relation: $1.0 \leq x \leq 1.3$; y represents an atomic ratio satisfying the following relation: $0 \leq y \leq 0.5$; and $\sigma$ represents an oxygen excess amount), wherein a specific surface area of the palladium-containing perovskite-type composite oxide is from 0.5 to 9.5 m²/g.

In the present invention, it is preferable that A in the general formula (1) is La.

In the present invention, it is preferable that B in the general formula (1) is at least one element selected from the group consisting of Fe and Co.

The method for synthesizing a compound of the present invention comprises reacting a compound represented by the general formula (2) with a compound represented by the general formula (3) or a compound represented by the general formula (4) in the presence of the above synthesis reaction catalyst:

$$R_1-X \tag{2}$$

wherein $R_1$ represents an aryl group which may have a substituent, a heterocyclic group which may have a substituent, or an alkenyl group which may have a substituent; and X represents a halogen atom, a trifluoromethanesulfonyloxy group, a p-toluenesulfonyloxy group or a methanesulfonyloxy group, $$R_2-M \tag{3}$$

wherein $R_2$ represents an aryl group which may have a substituent, a heterocyclic group which may have a substituent, or an alkenyl group which may have a substituent; M represents —B(ORa)₂— group or —Sn(Rb)₃ group; Ra represents a hydrogen atom or an alkyl group which may have a substituent; and Rb represents an alkyl group, and in stead of Ra, a ring including —OBO— may be formed through an arylene group which may have a substituent or an alkylene group which may have a substituent, both of which serve as a bond of —OBO—, and $$R_3HC=CR_4R_5 \tag{4}$$

wherein $R_3$, $R_4$ and $R_5$ each independently represents a hydrogen atom, an alkyl group which may have a substituent, an aryl group which may have a substituent, a carboxylic acid derivative, an acid amide derivative or a cyano group.

It is preferable that the method of synthesizing a compound of the present invention comprises reacting a compound represented by the general formula (2) with a compound represented by the general formula (3) in the presence of the synthesis reaction catalyst, $R_1$ is an aryl group which may have a substituent and X is a halogen atom in the general formula (2), and $R_2$ is an aryl group which may have a substituent and M is —B(ORa)₂ group in the general formula (3).

EFFECT OF THE INVENTION

The synthesis reaction catalyst of the present invention can synthesize a compound in a high yield due to an improvement in activity, and also can improve handling properties because the catalyst has small specific surface area and the particle size does not excessively decrease. Accordingly, the catalyst can be efficiently recovered and reused after the completion of the reaction.

Since the above synthesis reaction catalyst is used in the method of synthesizing a compound in the present invention, the compound can be synthesized in a high yield by a coupling reaction. Further, the synthesis reaction catalyst can be efficiently recovered and used repeatedly after the completion of the reaction.

DESCRIPTION OF THE INVENTION

The synthesis reaction catalyst of the present invention includes a palladium-containing perovskite-type composite oxide, which is represented by the following general formula (1):

$$A_x B_{(1-y)} Pd_y O_{3+\sigma} \qquad (1)$$

wherein A represents at least one element selected from rare earth elements and alkaline earth metals; B represents at least one element selected from transition elements (excluding rare earth elements and Pd) and Al; x represents an atomic ratio satisfying the following relation: $1.0 \leq x \leq 1.3$; y represents an atomic ratio satisfying the following relation: $0 < y \leq 0.5$; and σ represents an oxygen excess amount).

In the general formula (1), constituent elements of A are coordinated on the site A, while constituent elements of B and Pd are coordinated on the site B.

In the general formula (1), examples of the rare earth elements represented by A include Sc (scandium), Y (yttrium), La (lanthanum), Ce (cerium), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium) and Lu (lutetium), of which Y, La, Ce, Pr and Nd are preferred, and La is more preferred.

These rare earth elements can be used alone or in combination.

Further, in the general formula (1), examples of the alkaline earth metals represented by A include Be (beryllium), Mg (magnesium), Ca (calcium), Sr (strontium), Ba (barium) and Ra (radium).

These alkaline earth metals can be used alone or in combination.

In the present invention, the elements coordinated on the site A are preferably selected from rare earth elements. Further, an atomic ratio x of the elements (rare earth elements and/or alkaline earth metals) coordinated on the site A satisfies the following relation: $1.0 \leq x \leq 1.3$. When x is less than 1.0, it may be difficult to dissolve Pd to form a solid solution at a high rate stably. When x exceeds 1.3, by-products other than the perovskite-type composite oxide may be produced.

In the general formula (1), examples of transition elements excluding rare earth elements and Pd, which is represented by B, include elements having atomic numbers 22 (Ti) through 30 (Zn), atomic numbers of 40 (Zr) through 48 (Cd), and atomic numbers of 72 (Hf) through 80 (Hg) in the Periodic Table of Elements (IUPAC, 1990), excluding Pd.

These transition elements excluding rare earth elements and Pd can be used alone or in combination.

In the general formula (1), the elements coordinated on the site B include Pd as an essential element and preferably any elements selected from Cr (chromium), Mn (manganese), Fe (iron), Co (cobalt), Ni (nickel), Cu (copper), Zn (zinc) and Al (aluminum), of which Fe and Co are more preferred.

An atomic ratio y of Pd coordinated on the site B satisfies the following relation: $0 < y \leq 0.5$, that is, y is 0.5 or less. When the atomic ratio of Pd exceeds 0.5, it may be difficult to dissolve Pd to form a solid solution and also the cost is inevitably increased.

Therefore, on the site B, an element other than Pd (an element selected from transition elements excluding rare earth elements and Pd, and Al) is contained in an atomic ratio satisfying 1-y, that is to say, an atomic ratio satisfying the remainder of Pd (1-y) on the site B.

Further, σ represents an oxygen excess amount, and more specifically, it represents an excessive atomic ratio of oxygen that is generated as a result of excessive constituent elements on the site A as compared with A:B:O=1:1:3, which is a theoretical constituent ratio of the perovskite-type composite oxide represented by the general formula: $ABO_3$.

In the present invention, a specific surface area of the perovskite-type composite oxide is from 0.5 to 9.5 m²/g, and preferably from 1.0 to 5.0 m²/g. When the specific surface area is less than 0.5 m²/g, there arises a problem that reaction rate decreases, while when the specific surface area exceeds 9.5 m²/g, there arises such problems that reactivity decreases and handling properties deteriorate. Incidentally, a specific surface area can be calculated by a BET method.

The perovskite-type composite oxides can be prepared according to any suitable procedure for the preparation of composite oxide without any specific limitations. Examples thereof include a coprecipitation method, citrate complex method and alkoxide method.

In the coprecipitation method, for example, an aqueous mixed salt solution is prepared, which contains salts of the above-mentioned respective elements in the stoichiometric ratio, a neutralizing agent is added to the aqueous mixed salt solution and/or the aqueous mixed salt solution is added to the neutralizing agent for coprecipitation thereof, and the resulting coprecipitate is dried and subjected to heat treatment.

Examples of the salts of the respective elements include inorganic salts such as sulfates, nitrates, chlorides, and phosphates; and organic salts such as acetates and oxalates. The aqueous mixed salt solution can be prepared, for example, by adding the salts of the respective elements to water so as to establish a predetermined stoichiometric ratio and mixing them with stirring.

Then, the aqueous mixed salt solution is coprecipitated by adding the neutralizing agent thereto. Alternatively, a coprecipitate can be obtained by adding dropwise the aqueous mixed salt solution to an aqueous solution containing an excessive amount of neutralizing agent. The neutralizing agent includes, for example, ammonia; an organic base including amines such as triethylamine and pyridine; and an inorganic base such as sodium hydroxide, potassium hydroxide, potassium carbonate and ammonium carbonate. The neutralizing agent is added in an amount such that the pH of the resulting solution after the addition of the neutralizing agent is adjusted within a range about from 6 to 14, and preferably about from 8 to 12.

The resulting coprecipitate is washed with water, if necessary, dried by vacuum drying or forced-air drying, and subjected to a primary heat treatment at about 400 to 1,000° C., preferably at about 600 to 950° C., and furthermore subjected to a secondary heat treatment at about 900 to 1,100° C., if necessary. Thus, a perovskite-type composite oxide can be prepared.

In the citrate complex method, for example, an aqueous solution of a citrate salt mixture is prepared by mixing citric acid and salts of the respective elements in an amount establishing the predetermined stoichiometric ratio. The aqueous solution of the citrate salt mixture is thoroughly dried to form a citrate complex of the respective elements. The resulting citrate complex is provisionally baked and then subjected to a heat treatment.

Examples of the salts of the respective elements include the salts of the same kinds as those mentioned above. The aqueous solution of the citrate salt mixture is, for example, prepared by preparing an aqueous mixed salt solution in the same manner as above and adding an aqueous solution of citric acid to the aqueous mixed salt solution.

Then, the aqueous solution of the citrate salt mixture is thoroughly dried to form a citrate complex of the above-mentioned respective elements. The drying process is carried out at a temperature at which the formed citrate complex is not decomposed, for example, from room temperature to about 150° C. to remove water swiftly. Consequently, the above citrate complex of the respective elements can be formed.

The resulting citrate complex is then provisionally baked and heat treated. The provisional baking may be, for example, carried out at a temperature of 250° C. or more in vacuum or in an inert atmosphere. Then, the provisionally baked substance is subjected to a primary heat treatment at about 300 to 1,000° C., and preferably at about 600 to 950° C., and furthermore, followed by a secondary heat treatment at about 900 to 1,100° C. to obtain a perovskite-type composite oxide.

In the alkoxide method, for example, an alkoxide mixed solution is prepared, which contains alkoxides of the respective elements excluding Pd and other noble metals in the stoichiometric ratio. The alkoxide mixed solution is precipitated on hydrolysis by adding an aqueous solution containing salts of noble metals including Pd thereto. The resulting precipitate is dried and then subjected to a heat treatment.

Examples of the alkoxides of the respective elements include alcoholates each comprising the respective elements and an alkoxy such as methoxy, ethoxy, propoxy, isopropoxy or butoxy; and alkoxyalcoholates of the respective elements represented by the following general formula (5):

wherein E represents the respective elements; $R_6$ represents a hydrogen atom or an alkyl group having 1 to 4 carbon atoms; $R_7$ represents an alkyl group having 1 to 4 carbon atoms; i represents an integer of 1 to 3; and j represents an integer of 2 to 3.

More specific examples of the alkoxyalcoholates include methoxyethylate, methoxypropylate, methoxybutylate, ethoxyethylate, ethoxypropylate, propoxyethylate and butoxyethylate.

The alkoxide mixed solution is prepared, for example, by adding an alkoxide of the respective elements to an organic solvent in an amount that establishes the above stoichiometric ratio and mixing them with stirring.

The organic solvent is not specifically limited, as long as it can dissolve an alkoxide of the respective elements. Examples of such organic solvents include aromatic hydrocarbons, aliphatic hydrocarbons, alcohols, ketones and esters. Aromatic hydrocarbons such as benzene, toluene and xylene are preferred.

Then, the alkoxide mixed solution is precipitated by adding an aqueous solution containing salts of the noble metals including Pd in the predetermined stoichiometric ratio. Examples of the aqueous solution containing salts of the noble metals including Pd include an aqueous solution of nitrate, aqueous solution of chloride, aqueous solution of hexaammine chloride, aqueous solution of dinitrodiamine nitrate, aqueous solution of hexachloro acid hydrate and potassium cyanide salt.

The resulting precipitate is dried, for example, by vacuum drying or forced-air drying and is subjected to a primary heat treatment at about 400 to 1,000° C., preferably at about 500 to 850° C., and furthermore, followed by a secondary heat treatment at about 900 to 1,100° C. Thus, a perovskite-type composite oxide is prepared.

In such an alkoxide method, the composite oxide may be alternatively prepared in the following manner. A solution containing organometallic salts of the noble metals including Pd is added to the above-mentioned alkoxide mixed solution to prepare a homogenous mixed solution. The homogenous mixed solution is precipitated by adding water thereto. The resulting precipitate is dried and then subjected to a heat treatment.

Examples of the organometallic salts of the noble metals including Pd include: carboxylate of the noble metals including Pd, which is derived from acetate, propionate or the like; and metal chelate complexes of the noble metals including Pd such as diketone complexes of the noble metals including Pd, which is derived from diketone compounds represented by the following general formula (6) or (7):

$$R_8COCHR_{10}COR_9 \qquad (6)$$

wherein $R_8$ represents an alkyl group having 1 to 4 carbon atoms, a fluoroalkyl group having 1 to 4 carbon atoms or an aryl group; $R_9$ represents an alkyl group having 1 to 4 carbon atoms, a fluoroalkyl group having 1 to 4 carbon atoms, an aryl group or an alkyloxy group having 1 to 4 carbon atoms; and $R_{10}$ represents a hydrogen atom or an alkyl group having 1 to 4 carbon atoms; and $$CH_3CH(COR_{11})_2 \qquad (7)$$

wherein $R_{11}$ represents a hydrogen atom or an alkyl group having 1 to 4 carbon atoms.

In the above general formulas (6) and (7), examples of the alkyl group having 1 to 4 carbon atoms represented by $R_8$, $R_9$, $R_{10}$ and $R_{11}$ include methyl, ethyl, propyl, isopropyl, n-butyl, s-butyl and t-butyl. Examples of the fluoroalkyl group having 1 to 4 carbon atoms represented by $R_8$ and $R_9$ include trifluoromethyl. Examples of the aryl group represented by $R_8$ and $R_9$ include phenyl. Examples of the alkyloxy group having 1 to 4 carbon atoms represented by $R_9$ include methoxy, ethoxy, propoxy, isopropoxy, n-butoxy, s-butoxy and t-butoxy.

Specific examples of the diketone compound include 2,4-pentanedione, 2,4-hexanedione, 2,2-dimethyl-3,5-hexanedione, 1-phenyl-1,3-butanedione, 1-trifluoromethyl-1,3-butanedione, hexafluoroacetylacetone, 1,3-diphenyl-1,3-propanedione, dipivaloylmethane, methyl acetoacetate, ethyl acetoacetate and t-butyl acetoacetate.

The solution containing the organometallic salts of the noble metals including Pd can be prepared, for example, by adding an organometallic salt of the noble metals including Pd to an organic solvent in an amount that establishes the above-mentioned stoichiometric ratio, and mixing them with stirring. The organic solvent can be any of the above organic solvents.

The prepared solution containing organometallic salts of the noble metals including Pd is mixed with the above alkoxide mixed solution, and the resulting homogenous mixed solution is precipitated by adding water thereto. The resulting precipitate is dried by vacuum drying or forced-air drying, for example, and is subjected to a primary heat treatment at about 400 to 1,000° C., and preferably at about 500 to 850° C., and furthermore, followed by a secondary heat treatment at about 900 to 1,100° C. Thus, a perovskite-type composite oxide is prepared.

When a perovskite-type composite oxide is prepared in such a manner, the constituent materials of the perovskite-type composite oxide are baked at as high as 900 to 1,100° C. in the secondary heat treatment. This makes it possible for the obtained perovskite-type composite oxide contained in a synthesis reaction catalyst of the present invention to have a specific surface area of 0.5 to 9.5 m$^2$/g.

In the above preparation method of the composite oxide, the primary heat treatment and the secondary heat treatment are carried out separately. However, the treatments may be carried out together at one time.

Further, palladium may be further supported on the palladium-containing perovskite-type composite oxide. In order to further support palladium on the obtained palladium-containing perovskite-type composite oxide, known methods can be applied without any specific limitations. For example, the composite oxide may be prepared in the following manner. A solution containing salts including palladium is prepared, the solution is impregnated in a palladium-containing perovskite-type composite oxide, and baked. In this case, a supporting amount of palladium based on the palladium-containing perovskite-type composite oxide is, for example, 10 parts by weight or less, preferably from 0.1 to 5 parts by weight based on 100 parts by weight of the palladium-containing perovskite-type composite oxide.

In the palladium-containing perovskite-type composite oxide contained in a synthesis reaction catalyst of the present invention, those represented by the following general formula (8), among others, those represented by the following general formula (9), are preferably used.

$$A_v A'_w B_{(1-y)} Pd_y O_{3+\sigma} \qquad (8)$$

wherein A represents at least one element selected from rare earth elements; A' represents at least one element selected from alkaline earth metals; B represents at least one element selected from transition elements excluding rare earth elements and Pd, and Al; y represents an atomic ratio satisfying the following relation: $0 < y \leq 0.5$; w represents an atomic ratio satisfying the following relation: $0 \leq w \leq 0.5$; v represents an atomic ratio satisfying the following relation: $1.0 \leq v+w \leq 1.3$; and σ represents an oxygen excess amount.

$$A_x B_{(1-y)} Pd_y O_{3+\sigma} \qquad (9)$$

wherein A represents at least one element selected from Y, La, Ce, Pr and Nd; B represents at least one element selected from Mn, Fe, Co and Al; x represents an atomic ratio satisfying the following relation: $1.0 < x \leq 1.3$; y represents an atomic ratio satisfying the following relation: $0 < y \leq 0.5$; and σ represents an oxygen excess amount.

More specific examples of the palladium-containing perovskite-type composite oxide include $La_{1.00}Fe_{0.57}Co_{0.38}Pd_{0.05}O_3$, $La_{0.90}Ce_{0.10}Fe_{0.57}Co_{0.38}Pd_{0.05}O_3$, $La_{1.00}Fe_{0.95}Pd_{0.05}O_3$, $La_{1.00}Co_{0.95}Pd_{0.05}O_3$, $La_{0.90}Ce_{0.10}Al_{0.95}Pd_{0.05}O_3$, $La_{1.00}Fe_{0.57}Mn_{0.38}Pd_{0.05}O_3$, $La_{1.00}Mn_{0.95}Pd_{0.05}O_3$, $La_{1.05}Fe_{0.57}Co_{0.38}Pd_{0.05}O_{3+\sigma}$ and $La_{1.02}Fe_{0.95}Pd_{0.05}O_{3+\sigma}$ In the method of synthesizing a compound of the present invention, a compound represented by the following general formula (2) is reacted with a compound represented by the following general formula (3) or a compound represented by the following general formula (4) in the presence of the above synthesis reaction catalyst:

$$R_1-X \qquad (2)$$

wherein $R_1$ represents an aryl group which may have a substituent, a heterocyclic group which may have a substituent, or an alkenyl group which may have a substituent; and X represents a halogen atom, a trifluoromethanesulfonyloxy group, a p-toluenesulfonyloxy group or a methanesulfonyloxy group, $$R_2-M \qquad (3)$$

wherein $R_2$ represents an aryl group which may have a substituent, a heterocyclic group which may have a substituent, or an alkenyl group which may have a substituent; M represents —B(ORa)$_2$ group or —Sn(Rb)$_3$ group; Ra represents a hydrogen atom or an alkyl group which may have a substituent; and Rb represents an alkyl group, and in stead of Ra, a ring including —OBO— may be formed through an arylene group which may have a substituent or an alkylene group which may have a substituent, both of which serve as a bond of —OBO—, and $$R_3HC=CR_4R_5 \qquad (4)$$

wherein $R_3$, $R_4$ and $R_5$ each independently represents a hydrogen atom, an alkyl group which may have a substituent, an aryl group which may have a substituent, a carboxylic acid derivative, an acid amide derivative or a cyano group.

Examples of an aryl group of the aryl group which may have a substituent, which is represented by $R_1$ in the general formula (2), $R_2$ in the general formula (3) and $R_3$, $R_4$ and $R_5$ in the general formula (4), include aryl groups having 6 to 14 carbon atoms such as phenyl, tolyl, xylyl, biphenyl, naphthyl, anthryl, phenanthryl and azulenyl.

The substituent of the aryl group is not specifically limited, and examples of the substituent include such as hydrocarbon groups and hetero atom-containing hydrocarbon groups according to the purposes and applications. Examples thereof include alkyl groups having 1 to 4 carbon atoms such as methyl, ethyl, propyl, isopropyl, butyl, isobutyl, sec-butyl and tert-butyl; allenyl groups having 2 to 4 carbon atoms such as vinyl, 1-methylvinyl, 1-propenyl and allyl; alkynyl groups having 2 to 4 carbon atoms such as ethynyl, 1-propynyl and 1-propargyl; cycloalkyl groups having 3 to 6 carbon atoms such as cyclopropyl, cyclobutyl, cyclopentyl and cyclohexyl; cycloalkenyl groups having 5 to 7 carbon atoms such as cyclopentenyl and cyclohexenyl; aralkyl groups having 7 to 11 carbon atoms such as benzyl, α-methylbenzyl and phenethyl; phenyl group; alkoxy groups having 1 to 6 carbon atoms such as methoxy, ethoxy, propoxy, iso-propoxy, n-butoxy, iso-butoxy, sec-butoxy and tert-butoxy; phenoxy group; alkanoyl groups having 1 to 6 carbon atoms such as formyl, acetyl, propionyl, n-butyryl and iso-butyryl; benzoyl group; alkanoyloxy groups having 1 to 6 carbon atoms such as formyloxy, acetyloxy, propionyloxy, n-butyryloxy and iso-butyryloxy; benzoyloxy group; carboxyl group; alkoxycarbonyl groups having 2 to 7 carbon atoms such as methoxycarbonyl, ethoxycarbonyl, n-propoxycarbonyl, iso-propoxycarbonyl, n-butoxycarbonyl, isobutoxycarbonyl and tert-butoxycarbonyl; carbamoyl groups; N-mono-C$_{1-4}$ alkylcarbamoyl groups such as N-methylcarbamoyl, N-ethylcarbamoyl, N-propylcarbamoyl, N-isopropylcarbamoyl and N-butylcarbamoyl; N,N-di-C$_{1-4}$ alkylcarbamoyl groups such as N,N-dimethylcarbamoyl, N,N-diethylcarbamoyl, N,N-dipropylcarbamoyl and N,N-dibutylcarbamoyl; cyclic aminocarbonyl groups such as 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl; halogen atoms such as fluorine, chlorine, bromine and iodine; mono-, di- or tri-halogeno-C$_{1-4}$ alkyl groups such as chloromethyl, dichloromethyl, trifluoromethyl and trifluoroethyl; oxo group; amidino group; imino group; amino group; mono-$C_{1-4}$ alkylamino groups such as methylamino, ethylamino, propylamino, isopropylamino and butylamino; di-$C_{1-4}$ alkylamino groups such as dimethylamino, diethylamino, dipropylamino, diisopropylamino and dibutylamino; 3 to 6-membered cyclic amino groups containing carbon atoms, a nitrogen atom and optionally 1 to 3 hetero atoms selected from oxygen atom, sulfur atom, nitrogen atom and the like, such as aziridinyl, azetidinyl, pyrrolidinyl, pyrrolinyl, pyrolyl, imidazolyl, pyrazolyl, imidazolidinyl, piperidino, morpholino, dihydropyridyl, pyridyl, N-methylpiperazinyl and N-ethylpiperazinyl; alkanoyl amido groups having 1 to 6 carbon atoms such as formamide, acetamide, trifluoroacetamide, propionylamide, butyrylamide and isobutyrylamide; benzamide group; carbamoylamino group; N—$C_{1-4}$ alkylcarbamoylamino groups such as N-methylcarbamoylamino, N-ethylcarbamoylamino, N-propylcarbamoylamino, N-isopropylcarbamoylamino and N-butylcarbamoylamino; N,N-di-$C_{1-4}$ alkylcarbamoylamino groups such as N,N-dimethylcarbamoylamino, N,N-dimethylcarbamoylamino, N,N-dipropylcarbamoylamino and N,N-dibutylcarbamoylamino; alkylenedioxy groups having 1 to 3 carbon atoms such as methylenedioxy and ethylenedioxy; hydroxyl group; epoxy group (—O—); nitro group; cyano group; mercapto group; sulfo group; sulfino group; phosphono group; sulfamoyl group; monoalkylsulfamoyl groups having 1 to 6 carbon atoms such as N-methylsulfamoyl, N-ethylsulfamoyl, N-propylsulfamoyl, N-isopropylsulfamoyl, and N-butylsulfamoyl; di-$C_{1-4}$ alkylsulfamoyl groups such as N,N-dimethylsulfamoyl, N,N-diethylsulfamoyl, N,N-dipropylsulfamoyl and N,N-dibutylsulfamoyl; alkylthio groups having 1 to 6 carbon atoms such as methylthio, ethylthio, propylthio, isopropylthio, n-butylthio, sec-butylthio and tert-butylthio; phenylthio group; alkylsulfinyl groups having 1 to 6 carbon atoms such as methylsulfinyl, ethylsulfinyl, propylsulfinyl and butylsulfinyl; phenylsulfinyl group; alkylsulfonyl groups having 1 to 6 carbon atoms such as methylsulfonyl, ethylsulfonyl, propylsulfonyl and butylsulfonyl; and phenylsulfonyl group. The above groups may be substituted with 1 to 5 of these substituents.

Examples of a heterocyclic group of heterocyclic groups which may have a substituent represented by $R_1$ in the general formula (2) and $R_2$ in the general formula (3) include 5-membered cyclic groups containing, other than carbon atoms, 1 to 4 hetero atoms selected from oxygen atom, sulfur atom, nitrogen atom and the like, such as 2- or 3-thienyl, 2- or 3-furyl, 2- or 3-pyronyl, 2-, 3- or 4-pyridyl, 2-, 4- or 5-oxazolyl, 2-, 4- or 5-thiazolyl, 3,4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3, 4-thiadiazolyl, 4- or 5-(1,2,3-thiadiazolyl), 1,2,5-thiadiazolyl, 1,2,3-triazolyl, 1,2,4-triazolyl and 1H— or 2H-tetrazolyl; 6-membered cyclic groups containing, other than carbon atoms, 1 to 4 hetero atoms selected from oxygen atom, sulfur atom, nitrogen atom and the like, such as N-oxide-2-, 3- or 4-pyridyl, 2-, 4- or 5-pyrimidinyl, N-oxide-2-, 4- or 5-pyrimidinyl, thiomorpholinyl, morpholinyl, oxoimidazinyl, dioxotriazinyl, pyrrolidinyl, piperidinyl, pyranyl, thiopyranyl, 1,4-oxazinyl, 1,4-thiazinyl, 1,3-thiazinyl, piperadinyl, triazinyl, oxotriazinyl, 3- or 4-pyridazinyl, pyrazinyl and N-oxide-3- or 4-pyridazinyl; 5 to 8-membered rings or the condensed rings containing 1 to 4 hetero atoms such as oxygen atom, sulfur atom, nitrogen atom and the like, in addition to carbon atoms in a 2 or 3 cyclic condensed ring group which contains, other than carbon atoms, 1 to 4 hetero atoms selected from oxygen atom, sulfur atom, nitrogen atom and the like, such as benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthalazinyl, quinazolinyl, quinoxalinyl, indolizinyl, quinolizinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl and phenoxazinyl.

Substituents of the heterocyclic groups are not specifically limited, and examples include those corresponding to the purposes and applications, such as hydrocarbon group and hetero atom-containing hydrocarbon groups. For example, substituents of the same kinds as those mentioned above are properly included. The above groups may be substituted with 1 to 5 of these substituents.

Examples of an alkenyl group of alkenyl groups which may have a substituent represented by $R_1$ in the general formula (2) and $R_2$ in the general formula (3) include alkenyl groups having 2 to 18 carbon atoms such as vinyl, allyl, methallyl, isopropenyl, 1-propenyl, 2-propenyl, 2-methyl-1-propenyl, butenyl, pentenyl, hexenyl, heptynyl, octenyl, nonenyl, decenyl, undecenyl, dodecenyl, tetradecenyl, hexadecenyl and octadecenyl.

Substituents of the alkenyl groups are not specifically limited, and examples include those corresponding to the purposes and applications, such as hydrocarbon group and hetero atom-containing hydrocarbon groups. For example, substituents of the same kinds as those mentioned above are included. The substituents may be substituted with 1 to 5 heterocyclic groups.

Examples of an alkyl group of an alkyl group which may have a substituent represented by Ra in the general formula (3), an alkyl group represented by Rb and an alkyl group of an alkyl group which may have a substituent represented by $R_3$, $R_4$ and $R_5$ in the general formula (4) include alkyl groups having 1 to 18 carbon atoms such as methyl, ethyl, propyl, iso-propyl, n-butyl, iso-butyl, sec-butyl, tert-butyl, pentyl, iso-pentyl, sec-pentyl, hexyl, heptyl, n-octyl, isooctyl, 2-ethylhexyl, nonyl, decyl, isodecyl, dodecyl, tetradecyl, hexadecyl and octadecyl.

Substituents of the alkyl groups are not specifically limited, and examples include those corresponding to the purposes and applications, such as hydrocarbon group and hetero atom-containing hydrocarbon groups. For example, substituents of the same kinds as those mentioned above are included. The substituents may be substituted with 1 to 5 heterocyclic groups.

Examples of an arylene group which may have a substituent, which substitutes for Ra and serves as a bond of —OBO— to form a ring containing —OBO— in the general formula (3), include arylene groups having 6 to 10 carbon atoms such as phenylene, tolylene, xylylene and naphthylene.

Substituents of the arylene groups are not specifically limited, and examples include those corresponding to the purposes and applications, such as hydrocarbon group and hetero atom-containing hydrocarbon groups. For example, substituents of the same kinds as those mentioned above are included. The substituents may be substituted with 1 to 5 heterocyclic groups.

Examples of an alkylene group of an alkylene group which may have a substituent, which substitutes for Ra and serves as a bond of —OBO— to form a ring containing —OBO— in the general formula (3), include alkylene groups having 1 to 18 carbon atoms such as methylene, ethylene, propylene, iso-propylene, n-butylene, iso-butylene, sec-butylene, tert-butylene, pentylene, iso-pentylene, sec-pentylene, hexylene, heptylene, octylene, 2-ethylhexylene, nonylene, decylene, isodecylene, dodecylene, tetradecylene, hexadecylene and octadecylene.

Substituents of the alkylene groups are not specifically limited, and examples include those corresponding to the purposes and applications, such as hydrocarbon group and hetero atom-containing hydrocarbon groups. For example, substituents of the same kinds as those mentioned above are included. The substituents may be substituted with 1 to 5 heterocyclic groups.

When, in stead of Ra, a ring including —OBO— is formed through the above-mentioned arylene group or alkylene serving as a bond of —OBO—, the above general formula (3) turns into the following general formula (10):

[Chemical Formula 1]

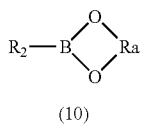

(10)

wherein $R_2$ represents an aryl group which may have a substituent, a heterocyclic group which may have a substituent or an alkenyl group which may have a substituent; and Ra represents an arylene group which may have a substituent or an alkylene group which may have a substituent.

More specifically, the general formula turns into the following general formula (11) when the arylene group which may have a substituent is phenylene, and it turns into the general formula (12) when the alkylene group which may have a substituent is 1,1,2,2-tetramethylethylene.

[Chemical Formula 2]

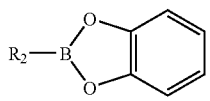

(11)

[Chemical Formula 3]

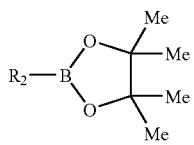

(12)

Examples of a halogen atom represented by X in the general formula (2) include chlorine, bromine and iodine.

Examples of carboxylic acid derivatives represented by $R_3$, $R_4$ and $R_5$ in the general formula (4) include alkoxycarbonyl groups such as methoxycarbonyl (—COOMe), ethoxycarbonyl (—COOEt) and t-butoxycarbonyl (—COOtBu).

In the general formula (4), more specific examples of compounds of such carboxylic acid derivatives are shown in Table 1.

TABLE 1

| $R_3$ | $R_4$ | $R_5$ | Name of compound | Structural formula |
|---|---|---|---|---|
| H | H | CO$_2$tBu | Tert-butyl acrylate | H$_2$C=CHCOOtBu |
| H | H | CO$_2$Me | Methyl acrylate | H$_2$C=CHCOOMe |
| H | H | CO$_2$Et | Ethyl acrylate | H$_2$C=CHCOOEt |
| Me | H | CO$_2$Et | Ethyl crotonate | MeCH=CHCOOEt |
| Me | Me | CO$_2$Et | Ethyl tiglate | MeCH=C(Me)COOEt |
| H | Me | CO$_2$Et | Ethyl methacrylate | H$_2$C=C(Me)COOEt |

Examples of acid amide derivatives represented by $R_3$, $R_4$ and $R_5$ in the general formula (4) include a carbamoyl (—CONH$_2$) group and N-mono or N,N-dialkylcarbamoyl groups such as N-methylcarbamoyl (—CONHMe) group and N,N-dimethylcarbamoyl (—CON(Me)$_2$) group.

In the general formula (4), more specific examples of compounds of such acid amide derivatives are shown in Table 2.

TABLE 2

| $R_3$ | $R_4$ | $R_5$ | Name of compound | Structural formula |
|---|---|---|---|---|
| H | H | CONH$_2$ | Acrylic acid amide | H$_2$C=CHCONH$_2$ |
| H | H | CONHMe | N-methylacrylic acid amide | H$_2$C=CHCONHMe |
| H | H | CONMe$_2$ | N,N-dimethylacrylic acid amide | H$_2$C=CHCONMe$_2$ |
| Me | H | CONHMe | N-methylcrotonic acid amide | MeCH=CHCONHMe |
| Me | Me | CONHMe | N-methyltiglic acid amide | MeCH=C(Me)CONHMe |
| H | Me | CONHMe | N-methylmethacrylic acid amide | H$_2$C=C(Me)CONHMe |

In the general formula (4), much more specific compounds wherein $R_3$, $R_4$ and $R_5$ are cyano groups are shown in Table 3.

TABLE 3

| $R_3$ | $R_4$ | $R_5$ | Name of compound | Structural formula |
|---|---|---|---|---|
| H | H | CN | Acrylonitrile | H$_2$C=CHCN |
| Me | H | CN | Crotononitrile | MeCH=CHCN |
| H | Me | CN | Methacrylonitrile | H$_2$C=C(Me)CN |

In the reaction of a compound represented by the above general formula (2) with a compound represented by the above general formula (3), a compound represented by the following general formula (13) is generated:

$$R_1\text{-}R_2 \qquad (13)$$

wherein $R_1$ and $R_2$ represent an aryl group which may have a substituent, a heterocyclic group which may have a substituent or an alkenyl group which may have a substituent.

In the general formula (13), an aryl group which may have a substituent, a heterocyclic group which may have a substituent or an alkenyl group which may have a substituent represented by $R_1$ and $R_2$ denote the same as above.

In the reaction of a compound represented by the above general formula (2) with a compound represented by the above general formula (3), when M in the general formula (3) is a —B(ORa)$_2$ group, the method of a synthesizing a compound of the present invention is given by the following reaction formula (14) called as Suzuki Cross-Couplings.

[Chemical Formula 4]

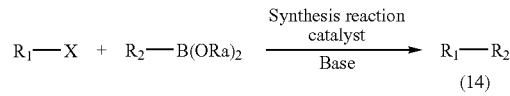

(14)

In the reaction of a compound represented by the above general formula (2) with a compound represented by the above general formula (3), when M in the general formula (3) is a —Sn(Rb)$_3$ group, the method of a synthesizing a compound by the present invention is given by the following reaction formula (15) called as Stille Cross-Couplings.

[Chemical Formula 5]

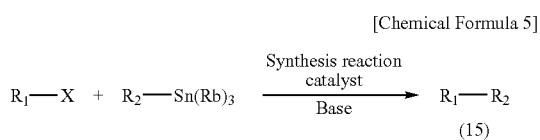

(15)

In the reaction of a compound represented by the above general formula (2) with a compound represented by the above general formula (4), a compound represented by the following general formula (16) is generated:

(16)

wherein $R_1$ represents an aryl group which may have a substituent, a heterocyclic group which may have a substituent or an alkenyl group which may have a substituent; $R_3$, $R_4$ and $R_5$ each independently represents a hydrogen atom, an alkyl group which may have a substituent, an aryl group which may have a substituent, a carboxylic acid derivative, an acid amide derivative or a cyano group.

In the general formula (16), an aryl group which may have a substituent, a heterocyclic group which may have a substituent or an alkenyl group which may have a substituent represented by $R_1$, and a hydrogen atom, an alkyl group which may have a substituent, an aryl group which may have a substituent, a carboxylic acid derivative, an acid amide derivative or a cyano group represented by $R_3$, $R_4$ and $R_5$ are the same as above.

In the method of a synthesizing a compound of the present invention, the reaction of a compound represented by the above general formula (2) with a compound represented by the above general formula (4) is given by the following reaction formula (17) called as Heck Cross-Couplings.

[Chemical Formula 6]

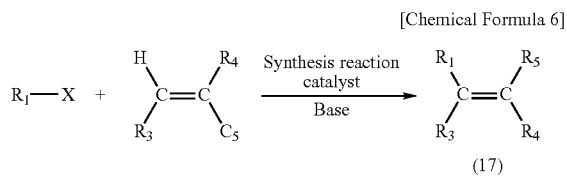

(17)

In the method of a synthesizing a compound of the present invention, in the above reaction formulas (14), (15) and (17), a compound represented by the above general formula (2) and a compound represented by the above general formula (3) or (4) are reacted in the presence of the above mentioned synthesis reaction catalyst and a base.

In this reaction, examples of the base include inorganic salts such as hydroxides such as sodium hydroxide and potassium hydroxide; carbonates such as sodium carbonate ($Na_2CO_3$), potassium carbonate ($K_2CO_3$) and cesium carbonate ($Cs_2CO_3$); acetates such as sodium acetate and potassium acetate; phosphates such as sodium phosphate ($Na_3PO_4$) and potassium phosphate ($K_3PO_4$); and organic salts such as ammonium salts such as triethylamines, pyridine, morphine, quinoline, piperidine, DBU (diazabicycloundecene), anilines and tetra-n-butylammonium acetate. These bases can be used alone or in combination.

In this reaction, a mixing ratio of the compound represented by the above general formula (2) to the compound represented by the above general formula (3) or (4) is not specifically limited. But, for example, the compound represented by the general formula (3) or (4) is mixed in an amount of 0.1 to 10 equivalents, and preferably 0.5 to 2 equivalents, based on the compound represented by the general formula (2).

Further, in this reaction, the palladium-containing perovskite-type composite oxide is added, although it is not specifically limited, for example, in an amount of 0.001 to 10 mol %, and preferably 0.001 to 5 mol %, in terms of palladium content.

In this reaction, the base is added, although it is not specifically limited, for example, in an amount of 1 to 30 equivalents, and preferably 1 to 10 equivalents.

The reaction is carried out, for example, under a reaction pressure of 0 to 5,000 KPa, and preferably from 0 to 3,000 KPa, at a reaction temperature of 0 to 250° C., and preferably from 0 to 150° C., for a reaction time of 0.1 to 72 hours, and preferably from 0.5 to 24 hours.

In this reaction, a reaction solvent may be used, and examples of the reaction solvent include water; and aqueous solvents such as alcohols such as methanol, ethanol and isopropanol; and alkoxy alcohols such as 2-methoxy-1-propanol, 2-ethoxy-1-propanol, ethylene glycol monomethyl ether (methyl cellosolve), ethylene glycol monoethyl ether (ethyl cellosolve) and ethylene glycol isopropyl ether. These reaction solvents can be used alone or in combination. Preferably, a mixture solvent of water/alcohols and a mixture solvent of water/alkoxy alcohols are used.

Further, in this reaction, an additive can be used in order to accelerate the reaction. Examples of the additive include organic ammonium halides such as tetra-n-butylammonium bromide (TBAB). The additive is added in an amount of, for example, 1 to 200 mol %.

More specifically, in this reaction, a compound represented by the above general formula (2) and a compound represented by the above general formula (3) or (4) are, together with the palladium-containing perovskite-type composite oxide and a base, added to a reaction solvent in the above ratio, and reacted under the above reaction conditions, thereby to obtain a compound represented by the above general formula (13) or (16).

In the method of synthesizing a compound of the present invention, Suzuki Cross-Couplings, Stille Cross-Couplings or Heck Cross-Couplings is carried out in the presence of the above mentioned synthesis reaction catalyst, which contains the palladium-containing perovskite-type composite oxide having a specific surface area of 0.5 to 9.5 $m^2$/g, and a compound represented by the above general formula (13) or (16) are synthesized in a high yield.

Since, in the method of synthesizing a compound of the present invention, the highly active palladium-containing perovskite-type composite oxide having a specific surface area of 0.5 to 9.5 $m^2$/g is used, a compound can be synthesized in a high yield.

Further, the synthesis reaction catalyst of the present invention has a specific surface area of 0.5 to 9.5 $m^2$/g, and therefore the particle size does not excessively decrease and handling properties can be improved. Consequently, after the reaction is completed, the catalyst can be easily recovered from the reaction mixture solution by means of filtration of decantation and reused.

In the method of synthesizing a compound of the present invention, a compound can be synthesized in a high yield and the reaction can be carried out repeatedly. Therefore, the method can be effectively used in applications using Suzuki Cross-Couplings on the industrial basis, for example, synthesis of drugs having the following biphenyl skeletons.

[Chemical Formula 7]

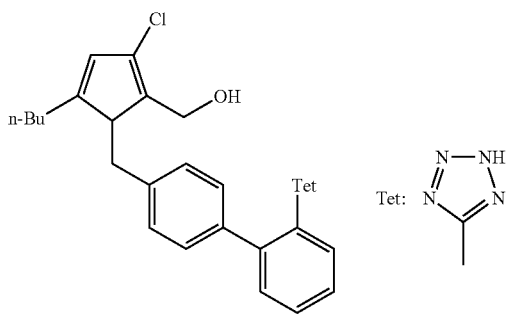

[Chemical Formula 8]

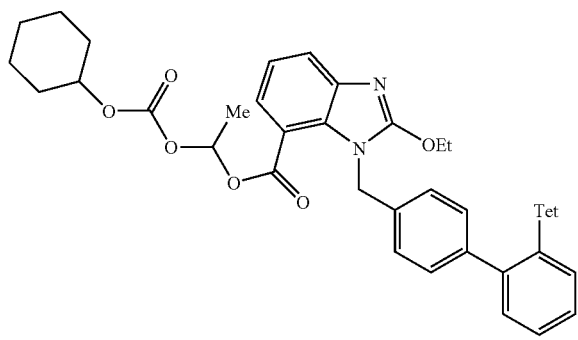

[Chemical Formula 9]

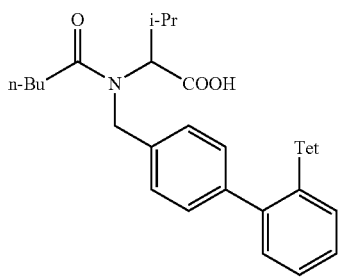

[Chemical Formula 10]

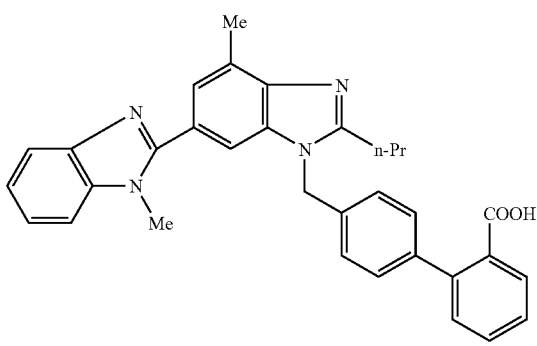

[Chemical Formula 11]

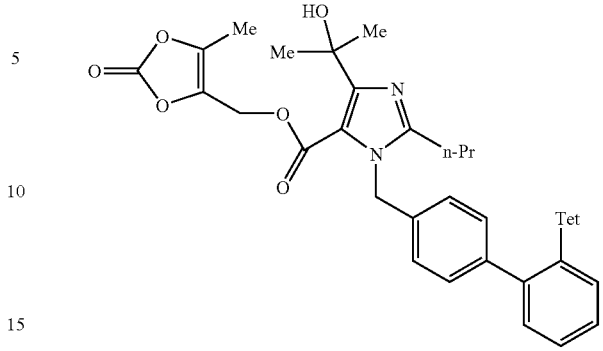

EXAMPLES

The present invention will now be described in more detail by way of Production Examples and Synthesis Examples, but are not limited thereto.

In the following Production Examples, the same operation was repeated 6 times to prepare the same powders to be used for 6 times, which were used for measurement of the specific surface area as described hereinafter. In Synthesis Examples by Suzuki Cross-Couplings described hereinafter, the powders prepared in Production Examples were subjected to a secondary heat treatment, thereby adjusting each specific surface area to that shown in Table 4

1) Production Examples of Synthesis Reaction Catalyst (Perovskite-Type Composite Oxide)

| Production Example 1 (Production of $La_{1.00}Fe_{0.57}Co_{0.38}Pd_{0.05}O_3$) | |
|---|---|
| Lanthanum methoxypropylate | 40.6 g (0.100 mol) |
| Iron methoxypropylate | 18.4 g (0.057 mol) |
| Cobalt ethoxyethylate | 9.0 g (0.038 mol) |

A mixed alkoxide solution was prepared by charging the above components in a 500 mL round-bottomed-flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFeCoPd.

Next, 200 mL of deionized water was added dropwise into the round-bottomed flask over about 15 minutes. A viscous brown precipitate was formed on hydrolysis.

After stirring at room temperature for 2 hours, the toluene and the water were distilled off under reduced pressure to obtain a precursor of the LaFeCoPd composite oxide. Then, the precursor was transferred into a petri dish, and subjected to forced-air drying at 60° C. for 24 hours, subjected to a primary heat treatment at 600° C. in the atmosphere for 2 hours using an electric furnace to obtain a blackish brown powder.

The X-ray powder diffraction of the powder was determined. The powder was identified as a single crystal phase including a composite oxide having a perovskite-type structure of $La_{1.00}Fe_{0.57}Co_{0.38}Pd_{0.05}O_3$. The specific surface area thereof was 30 m²/g.

| Production Example 2 (Production of $La_{1.05}Fe_{0.57}Co_{0.38}Pd_{0.05}O_{3+\sigma}$) | |
| --- | --- |
| Lanthanum methoxypropylate | 42.6 g (0.105 mol) |
| Iron methoxypropylate | 18.4 g (0.057 mol) |
| Cobalt ethoxyethylate | 9.0 g (0.038 mol) |

A mixed alkoxide solution was prepared by charging the above components in a 500 mL round-bottomed-flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFeCoPd.

Hereinafter, in the same manner as in Production Example 1, a blackish brown powder was obtained.

The X-ray powder diffraction of the powder was determined. The powder was identified as a single crystal phase including a composite oxide having a perovskite-type structure of $La_{1.05}Fe_{0.57}Co_{0.38}Pd_{0.05}O_{3+\sigma}$ The specific surface area thereof was 28 m²/g.

| Production Example 3 (Production of $La_{1.00}Fe_{0.95}Pd_{0.05}O_3$) | |
| --- | --- |
| Lanthanum methoxypropylate | 40.6 g (0.100 mol) |
| Iron methoxypropylate | 30.7 g (0.095 mol) |

A mixed alkoxide solution was prepared by charging the above components in a 500 mL round-bottomed-flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFePd.

Hereinafter, in the same manner as in Production Example 1, a blackish brown powder was obtained.

The X-ray powder diffraction of the powder was determined. The powder was identified as a single crystal phase including a composite oxide having a perovskite-type structure of $La_{1.00}Fe_{0.95}Pd_{0.05}O_3$. The specific surface area thereof was 38 m²/g.

| Production Example 4 (Production of $La_{1.02}Fe_{0.95}Pd_{0.05}O_{3+\sigma}$) | |
| --- | --- |
| Lanthanum methoxypropylate | 41.4 g (0.102 mol) |
| Iron methoxypropylate | 30.7 g (0.095 mol) |

A mixed alkoxide solution was prepared by charging the above components in a 500 mL round-bottomed-flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFePd.

Hereinafter, in the same manner as in Production Example 1, a blackish brown powder was obtained.

The X-ray powder diffraction of the powder was determined. The powder was identified as a single crystal phase including a composite oxide having a perovskite-type structure of $La_{1.02}Fe_{0.95}Pd_{0.05}O_{3+\sigma}$ The specific surface area thereof was 35 m²/g.

2) Measurement of Specific Surface Area

The respective powders to be used for 6 times obtained in Production Examples 1 to 4 were subjected to a secondary heat treatment under the conditions shown in Table 4, and the X-ray powder diffraction of the resulting powders were determined. As a result, the crystal phase of the respective powders were identified as a single crystal phase including a composite oxide having a perovskite-type structure of a composition that corresponds to respective Production Examples 1 to 4. The specific surface areas of the respective powders were calculated by a BET method. The results are shown in Table 4.

TABLE 4

| Composition of reaction synthesis catalyst | Temperature/time of secondary heat treatment | Specific surface area (m²/g) |
| --- | --- | --- |
| $La_{1.00}Fe_{0.57}Co_{0.38}Pd_{0.05}O_3$ | 600° C./2 hours | 30.0 |
| | 800° C./1 hour | 12.0 |
| | 900° C./1 hour | 4.3 |
| | 1,000° C./1 hour | 2.2 |
| | 1,100° C./1 hour | 1.6 |
| | 1,200° C./1 hour | 0.1 |
| $La_{1.05}Fe_{0.57}Co_{0.38}Pd_{0.05}O_{3+\sigma}$ | 600° C./2 hours | 28.0 |
| | 800° C./1 hour | 11.0 |
| | 900° C./1 hour | 4.0 |
| | 1,000° C./1 hour | 2.1 |
| | 1,100° C./1 hour | 1.3 |
| | 1,200° C./1 hour | 0.1 |
| $La_{1.00}Fe_{0.95}Pd_{0.05}O_3$ | 600° C./2 hours | 38.0 |
| | 800° C./1 hour | 17.0 |
| | 900° C./1 hour | 9.4 |
| | 1,000° C./1 hour | 5.0 |
| | 1,100° C./1 hour | 2.4 |
| | 1,200° C./1 hour | 0.1 |
| $La_{1.02}Fe_{0.95}Pd_{0.05}O_{3+\sigma}$ | 600° C./2 hours | 35.0 |
| | 800° C./1 hour | 14.0 |
| | 900° C./1 hour | 8.8 |
| | 1,000° C./1 hour | 4.9 |
| | 1,100° C./1 hour | 2.3 |
| | 1,200° C./1 hour | 0.1 |

3) Synthesis Example of 4-methoxybiphenyl by Suzuki Cross-Couplings

In the presence of each of the palladium-containing perovskite-type composite oxides which were prepared in Production Examples 1 to 4 and subjected to a secondary heat treatment as mentioned above so as to have a specific surface area shown in Table 4,4-bromoanisole and phenylboronic acid were reacted as shown in the following formula (18).

[Chemical Formula 12]

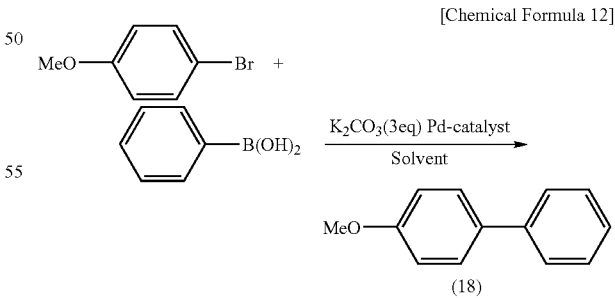

(18)

| 4-bromoanisole | 2.24 g (0.012 mol) |
| --- | --- |
| Phenylboronic acid | 2.19 g (0.018 mol) |
| Potassium carbonate | 4.98 g (0.036 mol) |

The above components were charged in a 100 mL round-bottomed flask, and then 18 mL of various alcohols and deionized water as a reaction solvent shown in Table 5 were each added and dissolved with stirring. The palladium-containing perovskite-type composite oxide prepared in each of Production Examples 1 to 4 was added to the solution in an amount shown in Table 5. The resulting solution was heated in a mantle heater, and then heated to reflux at a reflux temperature shown in Table 5 for 10 hours.

After the reaction was terminated, the flask was cooled, and 20 mL of toluene was added therein so as to dissolve the reaction product. Insoluble content was removed by suction filtration, and the toluene and the reaction solvent were distilled off under reduced pressure to precipitate a white solid product, and 20 mL of toluene and 20 mL of deionized water were added thereto to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-methoxybiphenyl as a white crystal. The weight of the obtained white crystal was measured to calculate the crude yield. It was 102 to 112%. Then, 20 mL of toluene was added to the white crystal to dissolve it with stirring, and the conversion rate was calculated according to the following equation using gas chromatography.

Conversion rate(%)=4-methoxybiphenyl/(4-bromoanisole+4-methoxybiphenyl)×100

(Each toluene solution of 4-methoxybiphenyl and 4-bromoanisole was measured to determine the relative sensitivity and a calibration correction was performed in advance.)

The results are shown in Table 5.

4) Measurement of Turnover Number

Aryl bromide (4-bromoanisole) represented by the above general formula (18) and boronic acid (phenylboronic acid) were reacted under the same reaction conditions as in Synthesis Examples. Using gas chromatography as mentioned above, the turnover number (TON) was calculated by the following equation in terms of mole number of the obtained 4-methoxybiphenyl per mol palladium.

Turnover number=4-methoxybiphenyl(mol)/palladium (mol)×conversion rate

The results are shown in Table 5.

TABLE 5

| | Pd-containing perovskite-type composite oxide | | | Reaction conditions | | | |
|---|---|---|---|---|---|---|---|
| | Composition | Specific surface area ($m^2/g$) | Addition amount (Pd mol %) | Reaction solvent* | Reflux temperature (°C.) | Conversion rate (%) | TON ($Pd^{-1}$) |
| Example 1 | $La_{1.00}Fe_{0.57}Co_{0.38}Pd_{0.05}O_3$ | 4.3 | 0.025 | MP/$H_2O$ | 100 | 96.3 | 3,852 |
| Example 2 | $La_{1.00}Fe_{0.57}Co_{0.38}Pd_{0.05}O_3$ | 2.2 | 0.025 | MP/$H_2O$ | 100 | 97.6 | 3,904 |
| Example 3 | $La_{1.00}Fe_{0.57}Co_{0.38}Pd_{0.05}O_3$ | 1.6 | 0.025 | MP/$H_2O$ | 100 | 95.8 | 3,832 |
| Example 4 | $La_{1.00}Fe_{0.57}Co_{0.38}Pd_{0.05}O_3$ | 4.3 | 0.025 | EGEE/$H_2O$ | 104 | 94.5 | 3,780 |
| Example 5 | $La_{1.00}Fe_{0.57}Co_{0.38}Pd_{0.05}O_3$ | 2.2 | 0.025 | EGEE/$H_2O$ | 104 | 96.0 | 3,840 |
| Example 6 | $La_{1.00}Fe_{0.57}Co_{0.38}Pd_{0.05}O_3$ | 1.6 | 0.025 | EGEE/$H_2O$ | 104 | 93.1 | 3,724 |
| Example 7 | $La_{1.05}Fe_{0.57}Co_{0.38}Pd_{0.05}O_{3+\sigma}$ | 4.0 | 0.025 | MP/$H_2O$ | 100 | 97.0 | 3,880 |
| Example 8 | $La_{1.05}Fe_{0.57}Co_{0.38}Pd_{0.05}O_{3+\sigma}$ | 2.1 | 0.025 | MP/$H_2O$ | 100 | 97.5 | 3,900 |
| Example 9 | $La_{1.05}Fe_{0.57}Co_{0.38}Pd_{0.05}O_{3+\sigma}$ | 1.0 | 0.025 | MP/$H_2O$ | 100 | 93.4 | 3,736 |
| Example 10 | $La_{1.00}Fe_{0.95}Pd_{0.05}O_3$ | 9.4 | 0.003 | MP/$H_2O$ | 100 | 93.3 | 31,099 |
| Example 11 | $La_{1.00}Fe_{0.95}Pd_{0.05}O_3$ | 5.0 | 0.003 | MP/$H_2O$ | 100 | 92.8 | 30,933 |
| Example 12 | $La_{1.00}Fe_{0.95}Pd_{0.05}O_3$ | 2.4 | 0.003 | MP/$H_2O$ | 100 | 90.8 | 30,267 |
| Example 13 | $La_{1.00}Fe_{0.95}Pd_{0.05}O_3$ | 9.4 | 0.003 | EGEE/$H_2O$ | 104 | 91.6 | 30,533 |
| Example 14 | $La_{1.00}Fe_{0.95}Pd_{0.05}O_3$ | 5.0 | 0.003 | EGEE/$H_2O$ | 104 | 92.2 | 30,733 |
| Example 15 | $La_{1.00}Fe_{0.95}Pd_{0.05}O_3$ | 2.4 | 0.003 | EGEE/$H_2O$ | 104 | 90.5 | 30,167 |
| Example 16 | $La_{1.00}Fe_{0.95}Pd_{0.05}O_3$ | 9.4 | 0.003 | EGME/$H_2O$ | 104 | 95.8 | 31,933 |
| Example 17 | $La_{1.00}Fe_{0.95}Pd_{0.05}O_3$ | 5.0 | 0.003 | EGME/$H_2O$ | 104 | 97.0 | 32,333 |
| Example 18 | $La_{1.00}Fe_{0.95}Pd_{0.05}O_3$ | 2.4 | 0.003 | EGME/$H_2O$ | 104 | 92.4 | 30,800 |
| Example 19 | $La_{1.02}Fe_{0.95}Pd_{0.05}O_{3+\sigma}$ | 8.8 | 0.003 | MP/$H_2O$ | 100 | 95.1 | 31,700 |
| Example 20 | $La_{1.02}Fe_{0.95}Pd_{0.05}O_{3+\sigma}$ | 4.9 | 0.003 | MP/$H_2O$ | 100 | 93.0 | 31,700 |
| Example 21 | $La_{1.02}Fe_{0.95}Pd_{0.05}O_{3+\sigma}$ | 2.4 | 0.003 | MP/$H_2O$ | 100 | 91.6 | 30,533 |
| Example 22 | $La_{1.00}Fe_{0.57}Co_{0.38}Pd_{0.05}O_3$ | 4.3 | 0.001 | EGME/$H_2O$ | 104 | 92.8 | 92,800 |
| Example 23 | $La_{1.00}Fe_{0.95}Pd_{0.05}O_3$ | 5.0 | 0.001 | EGME/$H_2O$ | 104 | 96.7 | 96,700 |
| Com. Example 1 | $La_{1.00}Fe_{0.57}Co_{0.38}Pd_{0.05}O_3$ | 30.0 | 0.025 | MP/$H_2O$ | 100 | 81.5 | 3,260 |
| Com. Example 2 | $La_{1.00}Fe_{0.57}Co_{0.38}Pd_{0.05}O_3$ | 12.0 | 0.025 | MP/$H_2O$ | 100 | 84.7 | 3,388 |
| Com. Example 3 | $La_{1.00}Fe_{0.57}Co_{0.38}Pd_{0.05}O_3$ | 0.1 | 0.025 | MP/$H_2O$ | 100 | 16.5 | 660 |
| Com. Example 4 | $La_{1.05}Fe_{0.57}Co_{0.38}Pd_{0.05}O_{3+\sigma}$ | 28.0 | 0.025 | MP/$H_2O$ | 100 | 80.4 | 3,216 |
| Com. Example 5 | $La_{1.05}Fe_{0.57}Co_{0.38}Pd_{0.05}O_{3+\sigma}$ | 11.0 | 0.025 | MP/$H_2O$ | 100 | 83.3 | 3,322 |
| Com. Example 6 | $La_{1.05}Fe_{0.57}Co_{0.38}Pd_{0.05}O_{3+\sigma}$ | 0.1 | 0.025 | MP/$H_2O$ | 100 | 53.2 | 2,128 |
| Com. Example 7 | $La_{1.00}Fe_{0.95}Pd_{0.05}O_3$ | 38.0 | 0.003 | MP/$H_2O$ | 100 | 82.5 | 27,500 |
| Com. Example 8 | $La_{1.00}Fe_{0.95}Pd_{0.05}O_3$ | 17.0 | 0.003 | MP/$H_2O$ | 100 | 84.3 | 28,100 |
| Com. Example 9 | $La_{1.00}Fe_{0.95}Pd_{0.05}O_3$ | 0.1 | 0.003 | MP/$H_2O$ | 100 | 45.0 | 15,000 |
| Com. Example 10 | $La_{1.02}Fe_{0.95}Pd_{0.05}O_{3+\sigma}$ | 35.0 | 0.003 | MP/$H_2O$ | 100 | 84.0 | 28,000 |
| Com. Example 11 | $La_{1.02}Fe_{0.95}Pd_{0.05}O_{3+\sigma}$ | 14.0 | 0.003 | MP/$H_2O$ | 100 | 84.7 | 28,233 |
| Com. Example 12 | $La_{1.02}Fe_{0.95}Pd_{0.05}O_{3+\sigma}$ | 0.1 | 0.003 | MP/$H_2O$ | 100 | 51.8 | 17,267 |
| Com. Example 13 | $La_{1.00}Fe_{0.57}Co_{0.38}Pd_{0.05}O_3$ | 12.0 | 0.001 | EGME/$H_2O$ | 104 | 80.3 | 80,300 |
| Com. Example 14 | $La_{1.00}Fe_{0.95}Pd_{0.05}O_3$ | 17.0 | 0.001 | EGME/$H_2O$ | 104 | 82.5 | 82,500 |

*MP: 2-methoxy-1-propanol EGEE: Ethylene glycol monoethyl ether (ethyl cellosolve) EGME: Ethylene glycol monomethyl ether (methyl cellosolve) IPA: Isopropyl alcohol 5) Synthesis Example of 4-acetylbiphenyl by Suzuki Cross-Couplings In the presence of each of the palladium-containing perovskite-type composite oxides which were prepared in Production Examples 1 to 4 and subjected to a secondary heat treatment as mentioned above so as to have a specific surface area shown in Table 4,4-bromoacetophenone and phenylboronic acid were reacted as shown in the following general formula (19).

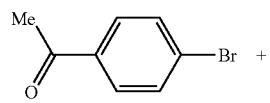

[Chemical Formula 13]

tive 4-acetylbiphenyl as a white crystal. The weight of the obtained white crystal was measured to calculate the crude yield. It was 101 to 108%. Then, 20 mL of tetrahydrofuran (THF) was added to the white crystal to dissolve it with stirring, and the conversion rate was calculated according to the following equation using gas chromatography.

Conversion rate (%)=4-acetylbiphenyl/(4-bromoacetophenone+4 acetylbiphenyl)×100

(Each toluene solution of 4-acetylbiphenyl and 4-bromoacetophenone was measured to determine the relative sensitivity and a calibration correction was performed in advance)

The results are shown in Table 6.

TABLE 6

|  | | Pd-containing perovskite-type composite oxide | | Reaction conditions | | | |
| --- | --- | --- | --- | --- | --- | --- | --- |
|  | Composition | Specific surface area (m$^2$/g) | Addition amount (Pd mol %) | Reaction solvent* | Reflux temperature (° C.) | Conversion rate (%) | TON (Pd$^{-1}$) |
| Example 24 | La$_{1.00}$Fe$_{0.57}$Co$_{0.38}$Pd$_{0.05}$O$_3$ | 4.3 | 0.001 | MP/H$_2$O | 100 | 97.2 | 97,200 |
| Example 25 | La$_{1.00}$Fe$_{0.95}$Pd$_{0.05}$O$_3$ | 5.0 | 0.001 | MP/H$_2$O | 100 | 100.0 | 100,000 |
| Com. Example 15 | La$_{1.00}$Fe$_{0.57}$Co$_{0.38}$Pd$_{0.05}$O$_3$ | 12.0 | 0.001 | MP/H$_2$O | 100 | 81.5 | 81,500 |
| Com. Example 16 | La$_{1.00}$Fe$_{0.95}$Pd$_{0.05}$O$_3$ | 17.0 | 0.001 | MP/H$_2$O | 100 | 88.5 | 88,500 |

*MP: 2-methoxy-1-propanol

-continued

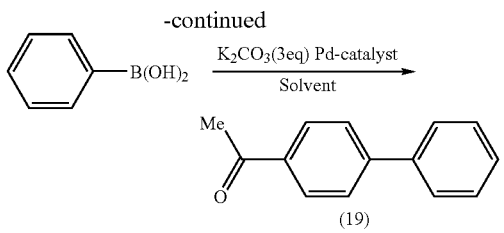

(19)

| 4-bromoacetophenone | 2.38 g (0.012 mol) |
| --- | --- |
| Phenylboronic acid | 2.19 g (0.018 mol) |
| Potassium carbonate | 4.98 g (0.036 mol) |

The above components were charged in a 100 mL round-bottomed flask, and then 18 mL of 2-methoxy-1-propanol and deionized water as a reaction solvent were each added and dissolved with stirring. Each of the palladium-containing perovskite-type composite oxide prepared in Production Examples 1 and 3 was added to the solution in an amount shown in Table 6. The resulting solution was heated in a mantle heater, and then heated to reflux at a reflux temperature shown in Table 6 for 4 hours.

After the reaction was terminated, the flask was cooled, and 50 mL of toluene was added therein so as to dissolve the reaction product. Insoluble content was removed by suction filtration, and the toluene and the reaction solvent were distilled off under reduced pressure to precipitate a white solid product, and 50 mL of toluene and 20 mL of deionized water were added thereto to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer and then it was shaken well. After dehydration and drying, insoluble matters were removed by filtration, and the solvent was distilled off from the filtrate to obtain the objec- 6) Synthesis Example of 4-methylbiphenyl by Suzuki Cross-Couplings In the presence of each of the palladium-containing perovskite-type composite oxides which were prepared in Production Examples 1 to 4 and subjected to a secondary heat treatment as mentioned above so as to have a specific surface area shown in Table 4,4-bromotoluene and triphenylboroxine were reacted as shown in the following general formula (20).

[Chemical Formula 14]

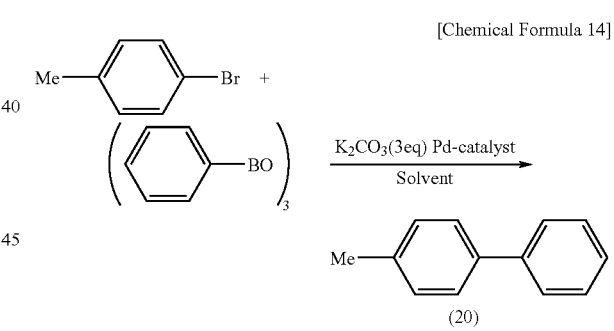

(20)

| 4-bromotoluene | 2.06 g (0.012 mol) |
| --- | --- |
| Triphenylboroxine | 1.86 g (0.006 mol) |
| Potassium carbonate | 4.98 g (0.036 mol) |

The above components were charged in a 100 mL round-bottomed flask, and then 18 mL of ethylene glycol monomethyl ether (methyl cellosolve) and deionized water as a reaction solvent were each added and dissolved with stirring. Each of the palladium containing perovskite-type composite oxide prepared in Production Examples 1 and 3 were added to the solution in an amount shown in Table 7. The resulting solution was heated in a mantle heater, and then heated to reflux at a reflux temperature shown in Table 7 for 4 hours.

After the reaction was terminated, the flask was cooled, and 20 mL of toluene was added therein so as to dissolve the reaction product. Insoluble content was removed by suction filtration, and the toluene and the reaction solvent were distilled off under reduced pressure to precipitate a white solid product, and 20 mL of toluene and 20 mL of deionized water were added thereto to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-methylbiphenyl as a white crystal. The weight of the obtained white crystal was measured to calculate the crude yield. It was 102 to 111%. Then, 20 mL of toluene was added to the white crystal to dissolve it with stirring, and the conversion rate was calculated according to the following equation using gas chromatography.

Conversion rate(%)4-methylbiphenyl/(4-bromotoluene+4-methylbiphenyl)×100

(Each toluene solution of 4-methylbiphenyl and 4-bromotoluene was measured to determine the relative sensitivity and a calibration correction was performed in advance)

The results are shown in Table 7.

| 4-bromoanisole | 2.26 g (0.012 mol) |
| 4-methylphenylboronic acid | 2.44 g (0.018 mol) |
| Potassium carbonate | 4.98 g (0.036 mol) |

The above components were charged in a 100 mL round-bottomed flask, and then 18 mL of 2-methoxy-1-propanol and deionized water as a reaction solvent were each added and dissolved with stirring. Each of the palladium-containing perovskite-type composite oxide prepared in Production Examples 1 and 3 was added to the solution in an amount shown in Table 8. The resulting solution was heated in a mantle heater, and then heated to reflux at a reflux temperature shown in Table 8 for 4 hours.

After the reaction was terminated, the flask was cooled, and 20 mL of toluene was added therein so as to dissolve the reaction product. Insoluble content was removed by suction filtration, and the toluene and the reaction solvent were dis-

TABLE 7

| | Pd-containing perovskite-type composite oxide | | | Reaction conditions | | | |
|---|---|---|---|---|---|---|---|
| | Composition | Specific surface area (m$^2$/g) | Addition amount (Pd mol %) | Reaction solvent* | Reflux temperature (° C.) | Conversion rate (%) | TON (Pd$^{-1}$) |
| Example 26 | La$_{1.00}$Fe$_{0.57}$Co$_{0.38}$Pd$_{0.05}$O$_3$ | 4.3 | 0.001 | EGME/H$_2$O | 104 | 100.0 | 100,000 |
| Example 27 | La$_{1.00}$Fe$_{0.95}$Pd$_{0.05}$O$_3$ | 5.0 | 0.001 | EGME/H$_2$O | 104 | 100.0 | 100,000 |
| Com. Example 17 | La$_{1.00}$Fe$_{0.57}$Co$_{0.38}$Pd$_{0.05}$O$_3$ | 12.0 | 0.001 | EGME/H$_2$O | 104 | 87.2 | 87,200 |
| Com. Example 18 | La$_{1.00}$Fe$_{0.95}$Pd$_{0.05}$O$_3$ | 17.0 | 0.001 | EGME/H$_2$O | 104 | 89.4 | 89,400 |

EGME: Ethylene glycol monomethyl ether (methyl cellosolve)

7) Synthesis Example of 4-methoxy-4'-methylbiphenyl by Suzuki Cross-Couplings

In the presence of each of the palladium-containing perovskite-type composite oxides which were prepared in Production Examples 1 to 4 and subjected to a secondary heat treatment as mentioned above so as to have a specific surface area shown in Table 4,4-bromoanisole and 4-methylphenylboronic acid were reacted as shown in the following general formula (21).

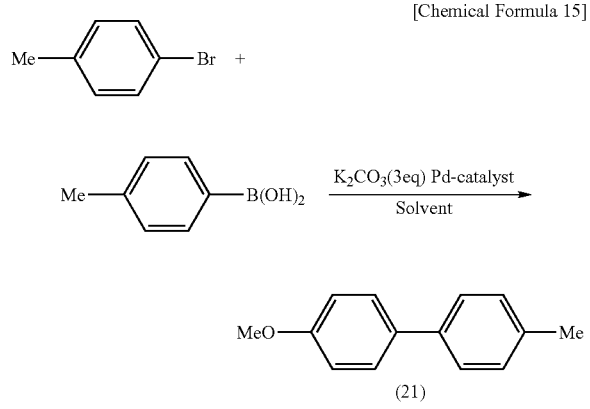

[Chemical Formula 15]

tilled off under reduced pressure to precipitate a white solid product, and 20 mL of toluene and 20 mL of deionized water were added thereto to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-methoxy-4'-methylbiphenyl as a white crystal. The weight of the obtained white crystal was measured to calculate the crude yield. It was 102 to 115%. Then, 20 mL of toluene was added to the white crystal to dissolve it with stirring and the conversion rate was calculated according to the following equation using gas chromatography.

Conversion rate(%)=4-methoxy-4'-methylbiphenyl/(4-bromoanisole+4-methoxy-4'-methylbiphenyl)×100

(Each toluene solution of 4-methoxy-4'-methylbiphenyl and 4-bromoanisole was measured to determine the relative sensitivity and a calibration correction was performed in advance)

The results are shown in Table 8.

TABLE 8

| | | Pd-containing perovskite-type composite oxide | | Reaction conditions | | | |
|---|---|---|---|---|---|---|---|
| | Composition | Specific surface area (m$^2$/g) | Addition amount (Pd mol %) | Reaction solvent* | Reflux temperature (° C.) | Conversion rate (%) | TON (Pd$^{-1}$) |
| Example 28 | La$_{1.00}$Fe$_{0.57}$Co$_{0.38}$Pd$_{0.05}$O$_3$ | 4.3 | 0.001 | MP/H$_2$O | 100 | 84.5 | 84,500 |
| Example 29 | La$_{1.00}$Fe$_{0.95}$Pd$_{0.05}$O$_3$ | 5.0 | 0.001 | MP/H$_2$O | 100 | 88.3 | 88,300 |
| Com. Example 19 | La$_{1.00}$Fe$_{0.57}$Co$_{0.38}$Pd$_{0.05}$O$_3$ | 12.0 | 0.001 | MP/H$_2$O | 100 | 67.6 | 67,600 |
| Com. Example 20 | La$_{1.00}$Fe$_{0.95}$Pd$_{0.05}$O$_3$ | 17.0 | 0.001 | MP/H$_2$O | 100 | 71.2 | 71,200 |

*MP: 2-methoxy-1-propanol

8) Synthesis Example of 4-nitrobiphenyl by Suzuki Cross-Couplings

In the presence of each of the palladium-containing perovskite-type composite oxides which were prepared in Production Examples 1 to 4 and subjected to a secondary heat treatment as mentioned above so as to have a specific surface area shown in Table 4, 4-bromonitrobenzene and phenylboronic acid were reacted as shown in the following general formula (22).

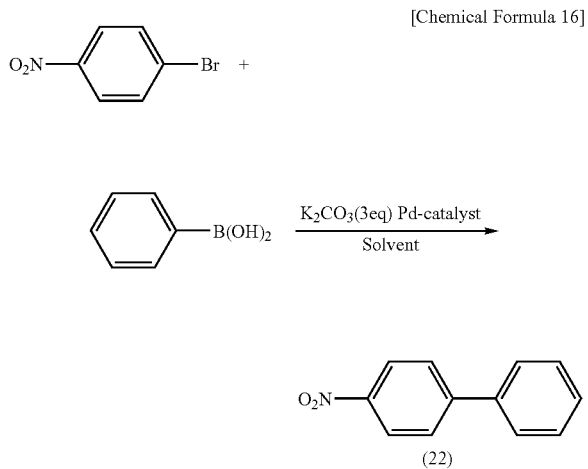

[Chemical Formula 16]

(22)

| 4-bromonitrobenzene | 2.42 g (0.012 mol) |
|---|---|
| Phenylboronic acid | 2.19 g (0.018 mol) |
| Potassium carbonate | 4.98 g (0.036 mol) |

The above components were charged in a 100 mL round-bottomed flask, and then 18 mL of ethylene glycol monomethyl ether (methyl cellosolve) and deionized water as a reaction solvent were each added and dissolved with stirring. The palladium-containing perovskite-type composite oxide prepared in Production Example 3 was added to the solution in an amount shown in Table 9. The resulting solution was heated in a mantle heater, and then heated to reflux at a reflux temperature shown in Table 9 for 4 hours.

After the reaction was terminated, the flask was cooled, and 20 mL of toluene was added therein so as to dissolve the reaction product. Insoluble content was removed by suction filtration, and toluene and the reaction solvent were distilled off under reduced pressure to precipitate a white solid product, and 20 mL of toluene and 20 mL of deionized water were added thereto to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-nitrobiphenyl as a yellow crystal. The weight of the obtained yellow crystal was measured to calculate the crude yield. It was 104 to 108%. Then, 20 mL of toluene was added to the yellow crystal to dissolve it with stirring, and the conversion rate was calculated according to the following equation using gas chromatography.

Conversion rate(%)=4-nitrobiphenyl/(4-bromonitrobenzene+4-nitrobiphenyl)×100

(Each toluene solution of 4-nitrobiphenyl and 4-bromonitrobenzene was measured to determine the relative sensitivity and a calibration correction was performed in advance)

The results are shown in Table 9.

TABLE 9

| | | Pd-containing perovskite-type composite oxide | | Reaction conditions | | | |
|---|---|---|---|---|---|---|---|
| | Composition | Specific surface area (m$^2$/g) | Addition amount (Pd mol %) | Reaction solvent* | Reflux temperature (° C.) | Conversion rate (%) | TON (Pd$^{-1}$) |
| Example 30 | La$_{1.00}$Fe$_{0.95}$Pd$_{0.05}$O$_3$ | 5.0 | 0.001 | EGME/H$_2$O | 104 | 100.0 | 100,000 |
| Com. Example 21 | La$_{1.00}$Fe$_{0.95}$Pd$_{0.05}$O$_3$ | 17.0 | 0.001 | EGME/H$_2$O | 104 | 83.5 | 83,500 |

EGME: Ethylene glycol monomethyl ether (methyl cellosolve)

9) Synthesis Example of 4-methoxybiphenyl by Stille Cross-Couplings

In the presence of each of the palladium-containing perovskite-type composite oxides which were prepared in Production Examples 1 to 4 and subjected to a secondary heat treatment as mentioned above so as to have a specific surface area shown in Table 4,4-bromoanisole and phenyltrimethyl tin were reacted as shown in the following general formula (23).

[Chemical Formula 17]

was distilled off from the filtrate to obtain the objective 4-methoxybiphenyl as a white crystal. The weight of the obtained white crystal was measured to calculate the crude yield. It was 102 to 110%. Then, 20 mL of toluene was added to the white crystal to dissolve it with stirring, and the conversion rate was calculated according to the following equation using gas chromatography.

Conversion rate(%)=4-methoxybiphenyl/(4-bromoanisole+4-methoxybiphenyl)×100

(Each toluene solution of 4-methoxybiphenyl and 4-bromoanisole was measured to determine the relative sensitivity and a calibration correction was performed in advance)

The results are shown in Table 10.

TABLE 10

| | Pd-containing perovskite-type composite oxide | | | Reaction conditions | | |
|---|---|---|---|---|---|---|
| | Composition | Specific surface area ($m^2/g$) | Addition amount (Pd mol %) | Reaction solvent* | Reflux temperature (°C.) | Conversion rate (%) | TON ($Pd^{-1}$) |
| Example 31 | $La_{1.00}Fe_{0.95}Pd_{0.05}O_3$ | 5.0 | 0.05 | $EGME/H_2O$ | 104 | 88.3 | 1,766 |
| Com. Example 22 | $La_{1.00}Fe_{0.95}Pd_{0.05}O_3$ | 17.0 | 0.05 | $EGME/H_2O$ | 104 | 65.5 | 1,310 |

EGME: Ethylene glycol monomethyl ether (methyl cellosolve)

-continued

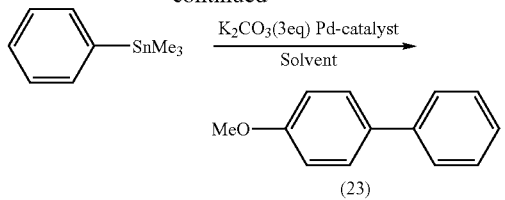

(23)

| 4-bromoanisole | 2.26 g (0.012 mol) |
|---|---|
| Phenyltrimethyl tin | 4.34 g (0.018 mol) |
| Potassium carbonate | 4.98 g (0.036 mol) |

The above components were charged in a 100 mL round-bottomed flask, and then 18 mL of ethylene glycol monomethyl ether (methyl cellosolve) and deionized water as a reaction solvent were each added and dissolved with stirring. The palladium-containing perovskite-type composite oxide prepared in Production Example 3 was added to the solution in an amount shown in Table 10. The resulting solution was heated in a mantle heater, and then heated to reflux at a reflux temperature shown in Table 10 for 8 hours.

After the reaction was terminated, the flask was cooled, and 20 mL of toluene was added therein so as to dissolve the reaction product. Insoluble content was removed by suction filtration, and toluene and the reaction solvent were distilled off under reduced pressure to precipitate a white solid product, and 20 mL of toluene and 20 mL of deionized water were added thereto to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent 10) Synthesis Example of tert-butyl 4-nitrophenyl Acrylate by Heck Cross-Couplings In the presence of each of the palladium-containing perovskite-type composite oxides which were prepared in Production Examples 1 to 4 and subjected to a secondary heat treatment as mentioned above so as to have a specific surface area shown in Table 4,4-bromonitrobenzene and tert-butyl acrylate were reacted as shown in the following general formula (24).

[Chemical Formula 18]

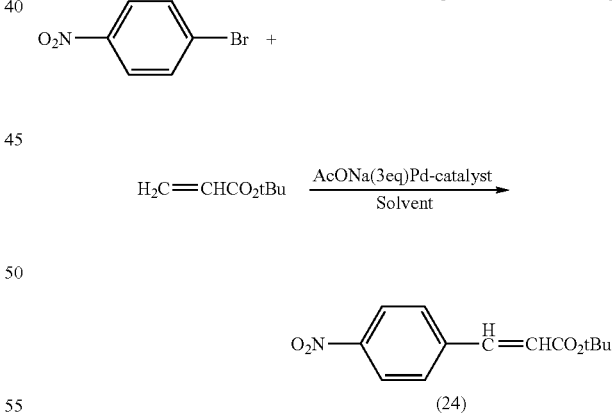

| 4-bromonitrobenzene | 2.42 g (0.012 mol) |
|---|---|
| Tert-butyl acrylate | 2.30 g (0.018 mol) |
| Sodium acetate | 2.88 g (0.036 mol) |

The above components were charged in a 100 mL round-bottomed flask, and then 60 mL of 2-methoxy-1-propanol as a reaction solvent were added and dissolved with stirring. The palladium-containing perovskite-type composite oxide prepared in Production Example 3 was added to the solution in an amount shown in Table 11. The resulting solution was heated in a mantle heater, and then heated to reflux at a reflux temperature shown in Table 11 for 6 hours.

After the reaction was terminated, the flask was cooled, and 40 mL of toluene was added therein so as to dissolve the reaction product. Insoluble content was removed by suction filtration, and toluene and the reaction solvent were distilled off under reduced pressure to precipitate a yellow solid product, and 40 mL of toluene and 20 mL of deionized water were added thereto to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective tert-butyl 4-nitrophenyl acrylate as a yellow crystal. The structure of the product was confirmed by GC-MS. The weight of the obtained yellow crystal was measured to calculate the crude yield. It was 104 to 112%. Then, 20 mL of tetrahydrofuran (THF) was added to the yellow crystal to dissolve it with stirring, and the conversion rate was calculated according to the following equation using gas chromatography.

Conversion rate(%)=tert-butyl 4-nitrophenyl acrylate/
(4-bromonitrobenzene+tert-butyl 4-nitrophenyl
acrylate)×100

(Each toluene solution of tert-butyl 4-nitrophenyl acrylate and 4-bromonitrobenzene was measured to determine the relative sensitivity and a calibration correction was performed in advance)

The results are shown in Table 11.

TABLE 11

| | Pd-containing perovskite-type composite oxide | | | Reaction conditions | | | |
| | Composition | Specific surface area (m²/g) | Addition amount (Pd mol %) | Reaction solvent* | Reflux temperature (° C.) | Conversion rate (%) | TON (Pd⁻¹) |
| --- | --- | --- | --- | --- | --- | --- | --- |
| Example 32 | La$_{1.00}$Fe$_{0.95}$Pd$_{0.05}$O$_3$ | 5.0 | 0.10 | MP | 122 | 97.4 | 974 |
| Com. Example 23 | La$_{1.00}$Fe$_{0.95}$Pd$_{0.05}$O$_3$ | 17.0 | 0.10 | MP | 122 | 79.6 | 796 |

*MP: 2-methoxy-1-propanol

While the illustrative embodiments and examples of the present invention are provided in the above description, such is for illustrative purpose only and it is not to be construed limitative. Modification and variation of the present invention which will be obvious to those skilled in the art is to be covered in the following claims.

INDUSTRIAL APPLICABILITY

As described above, the synthesis reaction catalyst of the present invention and the method of synthesizing a compound of the present invention are effectively applied when a palladium-containing perovskite-type composite oxide is used as a catalyst in a coupling reaction such as Suzuki Cross-Couplings, Stille Cross-Couplings or Heck Cross-Couplings.

The invention claimed is:
1. A method for synthesizing a compound, which comprises reacting a compound represented by the general formula (2) with a compound represented by the general formula (3) or a compound represented by the general formula (4) in the presence of a synthesis reaction catalyst which contains a palladium-containing perovskite-type composite oxide represented by the general formula (1) having a specific surface area of 0.5 to 5.0 m²/g:

$$A_xB_{(1-y)}Pd_yO_{3+\sigma} \quad (1)$$

wherein A represents La;

B represents Fe or FeCo;

x represents an atomic ratio satisfying the following relation: $1.0 \leq x \leq 1.3$;

y represents an atomic ratio satisfying the following relation: $0 < y \leq 0.5$; and σ represents an oxygen excess amount, $$R_1—X \quad (2)$$

wherein $R_1$ represents an aryl group which may have a substituent, a heterocyclic group which may have a substituent, or an alkenyl group which may have a substituent; and X represents a halogen atom, a trifluoromethanesulfonyloxy group, a p-toluenesulfonyloxy group or a methanesulfonyloxy group, $$R_2-M \quad (3)$$

wherein $R_2$ represents an aryl group which may have a substituent, a heterocyclic group which may have a substituent, or an alkenyl group which may have a substituent;

M represents —B(ORa)$_2$ group or —Sn(Rb)$_3$ group;

Ra represents a hydrogen atom or an alkyl group which may have a substituent; and Rb represents an alkyl group, and in stead of Ra, a ring including —OBO— may be formed through an arylene group which may have a substituent or an alkylene group which may have a substituent, both of which serve as a bond of —OBO—, and $$R_3HC=CR_4R_5 \quad (4)$$

wherein $R_3$, $R_4$ and $R_5$ each independently represents a hydrogen atom, an alkyl group which may have a substituent, an aryl group which may have a substituent, a carboxylic acid derivative, an acid amide derivative or a cyano group.

2. The method for synthesizing a compound according to claim 1, wherein the compound represented by the general formula (2) is reacted with the compound represented by the general formula (3) in the presence of the synthesis reaction catalyst, $R_1$ is an aryl group which may have a substituent and X is a halogen atom in the general formula (2), and $R_2$ is an aryl group which may have a substituent and M is —B(ORa)$_2$ group in the general formula (3).

* * * * *

UNITED STATES PATENT AND TRADEMARK OFFICE
CERTIFICATE OF CORRECTION

PATENT NO.        : 8,008,526 B2
APPLICATION NO.   : 11/886540
DATED             : August 30, 2011
INVENTOR(S)       : Hirohisa Tanaka and Kimiyoshi Kaneko It is certified that error appears in the above-identified patent and that said Letters Patent is hereby corrected as shown below:

ON THE TITLE PAGE:

- Item (73), the name of the assignee is corrected from: "Nitto Denko Corporation, Osaka (JP)" to --Daihatsu Motor Co., Ltd., Osaka (JP) and Hokko Chemical Industry Co., Ltd., Tokyo (JP)--.

- Item (57) (Abstract), in Chemical Formula 4, the three subtraction signs are incorrectly shown as long dashes, and the formula should read as follows:

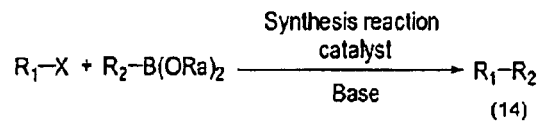

Signed and Sealed this
Fifteenth Day of November, 2011

David J. Kappos
*Director of the United States Patent and Trademark Office*

CERTIFICATE OF CORRECTION (continued)

(12) United States Patent
Tanaka et al.

(10) Patent No.: US 8,008,526 B2
(45) Date of Patent: Aug. 30, 2011

(54) SYNTHESIS REACTION CATALYST AND METHOD OF SYNTHESIZING COMPOUND USING THE SAME

(75) Inventors: Hirohisa Tanaka, Shiga (JP); Kimiyoshi Kaneko, Tokyo (JP)

(73) Assignee: Daihatsu Motor Co., Ltd., Osaka (JP) and Hokko Chemical Industry Co., Ltd., Tokyo (JP)

(*) Notice: Subject to any disclaimer, the term of this patent is extended or adjusted under 35 U.S.C. 154(b) by 896 days.

(21) Appl. No.: 11/886,540

(22) PCT Filed: Mar. 16, 2006

(86) PCT No.: PCT/JP2006/305204
§ 371 (c)(1),
(2), (4) Date: Sep. 17, 2007

(87) PCT Pub. No.: WO2006/098396
PCT Pub. Date: Sep. 21, 2006

(65) Prior Publication Data
US 2009/0023943 A1    Jan. 22, 2009

(30) Foreign Application Priority Data
Mar. 17, 2005  (JP) .................. 2005-077800

(51) Int. Cl.
*C07C 63/33*  (2006.01)
(52) U.S. Cl. ........... 562/492; 556/136; 556/7; 554/220
(58) Field of Classification Search .............. None
See application file for complete search history.

(56) References Cited

U.S. PATENT DOCUMENTS

| | | | |
|---|---|---|---|
| 7,411,082 B2 * | 8/2008 | Ley et al. | 556/136 |
| 2005/0215804 A1 * | 9/2005 | Ley et al. | 554/220 |

FOREIGN PATENT DOCUMENTS

| | | |
|---|---|---|
| EP | 1 533 274 A1 | 5/2005 |
| EP | 1 728 766 A1 | 12/2006 |
| WO | WO 2004/005194 | 1/2004 |
| WO | WO 2005/090238 | 9/2005 |

OTHER PUBLICATIONS

Takatoshi Ito et al., "Palladium-Catalyzed Cross-Coupling Reaction of Potassium Diaryldifluoroborates with Aryl Halides," Synlett, 2003, pp. 1435-1438, No. 10, Georg Thieme Chemistry, New York.
Olivier Baudoin et al., "Application of the Palladium-Catalyzed Borylation/Suzuki Coupling (BSC) Reaction to the Synthesis of Biologically Active Biaryl Lactams," Journal of Organic Chemistry, 2002, pp. 1199-1207, vol. 67, ACS Publications.
Stephen P. Andrews et al., "Heterogeneous or Homogeneous? A Case Study Involving Palladium-Containing Perovskites in the Suzuki Reaction," Advanced Synthesis & Catalysis, 2005, pp. 647-654, vol. 347, Wiley, Weinheim.
Isao Tan et al., "Structural Stability of Pd-Perovskite Catalysts after Heat Treatment Under Redox Condition," Journal of the Ceramic Society of Japan, 2005, pp. 71-76, vol. 113, Japan.
Tan, I et al., Structural Stability of Pd-Perovskite Catalysts after Heat Treatment Under Redox Condition, Journal of the Ceramic Society of Japan, 2005, vol. 113, No. 1313.
Martin D. Smith et al., Palladium-containing perovskites: recoverable and reuseable catalysts for Suzuki couplings, Chem. Comm., 2003, No. 21, UK.
Y. Nishihata et al., Self-regeneration of a Pd-perovskite catalyst for automotive emissions control, Nature, vol. 418, No. 6894, pp. 164-167, Jul. 2002, Japan.

* cited by examiner

*Primary Examiner* — Sudhakar Katakam
(74) *Attorney, Agent, or Firm* — Jean C. Edwards, Esq.; Edwards Neils PLLC

(57) ABSTRACT

To improve a catalytic activity of a composite oxide, to carry out a reaction in a high yield, and to provide a synthesis reaction catalyst having excellent handling properties and a method of a synthesizing a compound using the same, a synthesis reaction catalyst containing a palladium-containing perovskite-type composite oxide having a specific surface area of 0.5 to 9.5 m²/g is used in Suzuki Cross-Couplings given by the following general scheme (14).

[Chemical Formula 4]

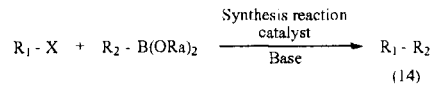

(14)

2 Claims, No Drawings